United States Patent
Ben Ouada et al.

(10) Patent No.: US 11,007,133 B2
(45) Date of Patent: *May 18, 2021

(54) METHOD FOR PRODUCING A STABLE PRECIPITATE ENRICHED IN PHYCOBILIPROTEINS

(71) Applicant: ALGOBIOTECH, Evry (FR)

(72) Inventors: Hatem Ben Ouada, Evry (FR); Jihene Ammar, Evry (FR)

(73) Assignee: ALGOBIOTECH, Evry (FR)

(*) Notice: Subject to any disclaimer, the term of this patent is extended or adjusted under 35 U.S.C. 154(b) by 167 days.

This patent is subject to a terminal disclaimer.

(21) Appl. No.: 15/505,932

(22) PCT Filed: Aug. 28, 2015

(86) PCT No.: PCT/FR2015/052293
§ 371 (c)(1),
(2) Date: Feb. 23, 2017

(87) PCT Pub. No.: WO2016/030643
PCT Pub. Date: Mar. 3, 2016

(65) Prior Publication Data
US 2017/0305966 A1 Oct. 26, 2017

(30) Foreign Application Priority Data
Aug. 28, 2014 (FR) .................................... 1401918

(51) Int. Cl.
*C07K 1/30* (2006.01)
*A61K 8/64* (2006.01)
(Continued)

(52) U.S. Cl.
CPC ............ *A61K 8/645* (2013.01); *A23L 33/195* (2016.08); *A61K 8/9717* (2017.08);
(Continued)

(58) Field of Classification Search
None
See application file for complete search history.

(56) References Cited

U.S. PATENT DOCUMENTS

| 4,320,050 A | 3/1982 | Rebeller et al. |
| 5,643,585 A | 7/1997 | Arad et al. |
| 2015/0239941 A1 | 8/2015 | Pottecher |

FOREIGN PATENT DOCUMENTS

| CN | 1 438 240 A | 8/2003 |
| FR | 2453199 A1 | 10/1980 |

(Continued)

OTHER PUBLICATIONS

Cuellar-Bermudez et al., Extraction and purification of high-value metabolites from microalgae: essential lipids, astaxanthin and phycobiliproteins, Microbial Btiotechnology (2015) 8(2) 190-209.*
Biswal et al., Chloroplast Biogenesis: From Proplastid to Gerontoplast, (2003). Google books (online p. 127).*
Chaiklahan et al., Stability of phycocyanin extracted from *Spirulina* sp.: Influence of temperature, pH, and preservatives, Process Biochemistry 47 (2012) 659-664.*

(Continued)

*Primary Examiner* — Erin M. Bowers
(74) *Attorney, Agent, or Firm* — MH2 Technology Law Group LLP

(57) ABSTRACT

The invention relates to a novel method for producing a stable precipitate enriched in phycobiliproteins by means of salicylic acid precipitation. The invention also relates to the use of said precipitate enriched in phycobiliproteins for producing cosmetic or dermatological, and food or nutraceutical compositions.

13 Claims, 1 Drawing Sheet

(51) Int. Cl.
| | |
|---|---|
| A61K 35/748 | (2015.01) |
| C07K 14/405 | (2006.01) |
| A61Q 19/08 | (2006.01) |
| A61Q 19/00 | (2006.01) |
| A61K 38/16 | (2006.01) |
| A61Q 17/04 | (2006.01) |
| A61Q 19/02 | (2006.01) |
| C07K 14/195 | (2006.01) |
| A61K 8/9717 | (2017.01) |
| A23L 33/195 | (2016.01) |

(52) U.S. Cl.
CPC .......... *A61K 35/748* (2013.01); *A61K 38/164* (2013.01); *A61Q 17/04* (2013.01); *A61Q 19/005* (2013.01); *A61Q 19/02* (2013.01); *A61Q 19/08* (2013.01); *C07K 1/30* (2013.01); *C07K 14/195* (2013.01); *C07K 14/405* (2013.01); *A23V 2002/00* (2013.01); *A61K 2800/522* (2013.01)

(56) References Cited

FOREIGN PATENT DOCUMENTS

| WO | 2005/065697 A1 | | 7/2005 |
|---|---|---|---|
| WO | WO 2005/065697 | * | 7/2005 |
| WO | 2014/045177 A1 | | 3/2014 |

OTHER PUBLICATIONS

Silveira et al., Optimization of phycocyanin extraction from Spirulina platensis using factorial design, Bioresource Technology 98 (2007) 1629-1634.*

Padgett et al., Large scale preparation of pure phycobiliproteins, Photosynthesis Research 11: 225-235 (1987).*

Donald A. Bryant et al., "Characterization and Structural Properties of the Major Biliproteins of *Anabaena* sp.", Archives of Microbiology, vol. 110, 1976, pp. 61-75.

Jorge Alberto Vieira Costa et al., "Modelling of Spirulina platensis growth in fresh water using response surface methodology", World Journal of Microbiology & Biotechnology, vol. 18, 2002, pp. 603-607.

* cited by examiner

METHOD FOR PRODUCING A STABLE PRECIPITATE ENRICHED IN PHYCOBILIPROTEINS

TECHNICAL FIELD

The present disclosure relates to a process for obtaining a stable precipitate enriched in phycobiliproteins, from algae.

More particularly, the present disclosure relates to a process for obtaining a stable and phycobiliprotein-enriched precipitate, comprising at least one precipitation step consisting of the addition of salicylic acid to an aqueous extract of phycobiliproteins, said precipitate having a phycobiliprotein content at least equal to 50% of the amount initially contained in said aqueous extract, and having a clarity at least equal to 70%. Phycobiliproteins, among which are distinguished phycocyanins, phycoerythrins, allophycocyanins and the proteins associated therewith, are photosynthetic pigmentary proteins present in certain algae (red algae and Cryptophyceae) and in all cyanobacteria. These protein pigments have a coloring capacity ranging from red to blue.

BACKGROUND

Currently, these pigments are experiencing a renewed interest. There is in fact at the current time a strong trend toward replacing synthetic components with natural products. This trend is explained, on the one hand, by the increase in consumer demand for natural products for health, ecological and environmental protection demands and, on the other hand, by the change in legislation which aims to promote natural products over synthetic products. This situation explains the considerable increase in market demand for natural dyes.

A review of the list of natural dyes available on the market reveals a considerable lack of blue dyes. The only ones indicated are chamazulene (extracted from chamomile flowers) and indigo (resulting from the fermentation of indigo plant leaves). The availability of these two dyes remains however below market needs, owing to low extraction yields which, for both, do not exceed 0.1% of the dry weight.

Among the phycobiliproteins, phycocyanin holds a de facto monopoly owing to its unique blue color. Phycocyanin is a colored protein found exclusively in blue algae. It cannot be synthesized chemically. The results of various studies relating to phycocyanin make reference to the possibility of its antioxidant, anti-inflammatory and anti-tumor capacity.

Phycocyanin is widely indicated for coloring certain food products blue (ices or sweet products of the type iced drinks, ice creams, doughs, cakes and cookies, etc.).

It can be introduced as a component into skin care creams, beauty masks and sun products. It advantageously replaces synthetic pigments considered to be suspect.

At the current time, the known applications of phycocyanin on an industrial scale are limited to a few food products (marzipans; sweet juices; ices, sorbets and incidentally chocolates) or to a few cosmetic formulations (creams and gels). The only sales of phycocyanin on the market are monopolized by a few companies (essentially Japanese) and manage to cover only 2% at most of the American market of natural food dyes.

Furthermore, phycocyanin can be extracted from the cyanobacterium *spirulina* (*Arthrospira platensis*), which can contain from 3% to 12% of phycocyanin. This blue microalga, considered by the WHO to be SAFE, is produced on an industrial scale. Its exploitation is widespread in several countries throughout the world.

Once phycobiliproteins have been extracted from biomass, it is necessary to carry out a concentrating step which usually results in a precipitation.

There are several phycobiliprotein concentrating processes. Some are lengthy using heavy equipment, such as centrifugation, lyophilization or else dialysis. The extrapolation of such processes on an industrial scale generates high investment costs. Others, which are simpler, use precipitation with salts and particularly ammonium sulfate which makes it possible, in addition, to preserve the phycobiliproteins against bacteria and fungi. In the context of a precipitation with ammonium sulfate, high amounts of this salt (greater than 60% of the weight of the extract) are required. Furthermore, ammonium sulfate is known for its acute effects of skin and eye irritation and of pulmonary congestion and respiratory difficulties in the event of ingestion or inhalation.

Excluded from this context are the other methods commonly used to precipitate proteins, which employ acids, organic solvents, nonionic polymers or even flocculating agents which are non-food-grade, and often cause denaturation of the phycobiliproteins.

U.S. Pat. No. 5,643,585 proposes using a material derived from red algae, in insoluble, more stable form; said material being obtained by means of a process using an organic solvent. This insoluble form limits the use of these pigments to powdered compounds.

Patent WO 2005/065697 describes a process for photostabilization of phycobiliproteins by adding an excipient containing ascorbic add to the aqueous extract. This process describes no step of concentrating the extract which is essential for preparations requiring a low water content.

Patent WO 2014/045177 describes a process for extracting and stabilizing phycocyanin by direct maceration of the biomass in glycerol or in a water/glycerol mixture, followed by filtration. The maceration time required is quite long, ranging up to 15 days. Likewise, the extraction yield is quite low, not exceeding 1% of the biomass used.

SUMMARY

The inventors have demonstrated that the addition of salicylic acid to an aqueous extract of phycobiliproteins makes it possible to precipitate the phycobiliproteins. Salicylic acid is a natural acid, of food quality and very commonly used as a food preservative.

The main requirements of the phycobiliprotein market cover three essential aspects: the need to respond to the various legislations relating to food or cosmetic products, good stability of the color and a competitive price. The natural nature of phycobiliproteins in general, and the fact that their extraction is carried out in aqueous solution, in the absence of any organic solvent, is a definite advantage in terms of the legislation.

The technical problem that the disclosure seeks to solve is that of obtaining a precipitate which is rich in phycobiliproteins while at the same time being stable.

Phycobiliproteins are protein in nature, soluble in aqueous solvents, thereby promoting the development of bacteria and fungi and seriously affecting their shelf life. Phycobiliproteins are, moreover, strongly photosensitive, which causes poor color stability, limiting bulk industrial use of these phycobiliproteins. Indeed, phycobiliproteins are subject to photodegradation which makes them rapidly lose their coloring capacity even under weak illumination. This photochemical process results in partial or total denaturation of the chromophore molecule. Some processes use oxygen scavengers and free radical scavengers, such as biopterin-glucoside. The phycobiliproteins are chemically conjugated to these scavengers. Such stabilizers are not, up until now time, entirely satisfactory because there is no certainty regarding their non-toxicity. Moreover, their cost is too high to envision use on a large scale regardless of the final use of the phycobiliproteins.

Finally, the phycobiliproteins stabilized up until now are stabilized only over a short period of time (a few hours), incompatible with a cosmetic, nutraceutical or food-processing application of these pigments.

The inventors have surprisingly demonstrated that the addition of salicylic acid to an aqueous extract of phycobiliproteins makes it possible to solve the technical problem addressed.

The subject of the disclosure is thus a process for obtaining a stable precipitate enriched in phycobiliproteins, comprising at least one precipitation step consisting of the addition of salicylic acid to an aqueous extract of phycobiliproteins, said precipitate having a phycobiliprotein content at least equal to 50% of the amount initially contained in said aqueous extract and having a clarity at least equal to 70%.

The term "phycobiliproteins" is intended to mean photosynthetic water-soluble pigmentary proteins such as allophycocyanin (APC), the phycocyanin family (C-PC and R-PC), the phycoerythrin family (R-PE and C-PE) and phycoerythrocyanin (PEC), isolated from certain microalgae or from cyanobacteria.

The term "aqueous extract" is intended to mean the product obtained by means of the step of extraction and dissolution of phycobiliproteins using an aqueous solvent such as water, sea water or any aqueous solution containing $CaCl_2$, NaCl or any other phosphate or potassium salt.

The term "precipitate", which results from the precipitation step, is intended to mean namely the amount of phycobiliproteins concentrated by precipitation, from an aqueous extract. In the context of the disclosure, salicylic acid is used to precipitate the phycobiliproteins.

The term "stable" is intended to mean a precipitate in which the phycobiliproteins are not degraded, in particular not degraded in natural light. The stability can be measured by the half-life of the phycobiliproteins, which represents the number of days resulting in degradation of half the phycobiliproteins.

The half-life of phycobiliproteins precipitated by means of the process of the present disclosure can reach 50, 60, 70, 80, 90, 100 or even 110 days for a temperature below 20° C., in particular a temperature of between 10 and 20° C., and a light intensity of less than 50 µmol $m^{-2}$ $s^{-1}$, in particular a light intensity of between 5 µmol $m^{-2}s^{-1}$ and 50 µmol $m^{-2}$ $s^{-1}$.

The half-life is for example determined according to the concentration of phycobiliproteins as a function of days (or of hours). The degree of phycobiliprotein degradation is then expressed in the following way: ((initial amount of phycobiliproteins−amount of phycobiliproteins on day d)×100/initial amount of phycobiliproteins). The half-life corresponds to the number of days where half (50%) of the initial concentration is degraded, i.e. this degree is equal to 50%. In the case where the degradation is low and does not reach 50%, it is possible to extrapolate using the daily degree of degradation obtained in the experimental range in order to predict the half-life outside the range.

The stability can also be evaluated by the maintaining of the color. Indeed, any decomposition of phycobiliproteins will lead to a change in color of the suspension or of the extract.

The color can be evaluated by measuring the absorbance of the extract at 620 nm for example, corresponding to the peak of absorption of the phycobiliproteins. A decrease in absorbance at this wavelength indicates a degradation of the phycobiliproteins.

A biomass of microalgae contains at most, depending on the culture conditions, 20% to 25% of phycobiliproteins. Consequently, the expression "precipitate having a phycobiliprotein content at least equal to 50% of the amount initially contained in the aqueous extract" is intended to mean the fact that 50% of the 20% to 25% of the phycobiliproteins that the aqueous extract contains are precipitated by the process according to the disclosure.

The phycobiliproteins which are the subject of the present disclosure can be extracted from cyanobacteria or from microalgae.

Said microalgae are in particular chosen from rhodophyceae, cryptophyceae and cyanobacteria, more particularly cyanobacteria, even more particularly *Arthrospira platensis* and *Aphanizomenon flos-aquae*, in particular the alga Klamath.

When the extraction is made on *Arthrospira platensis* (*spirulina*), it is carried out according to the process described by M. Rebeller et al., 1979. This extraction process is carried out in a solution of $CaCl_2$ at 10 g/l for two hours, which is followed by a filtration through 10 µm gauze. It can also be carried out in sea water, which makes it possible to enrich the phycobiliprotein extract in trace elements and to reduce the cost of extraction by avoiding the use of commercial salts.

The amount of the various phycobiliproteins in solution is determined by the spectrophotometric method established by Bryant et al., 1976.

The process according to the present disclosure makes it possible to obtain a phycobiliprotein precipitate comprising at least 50% of the amount of phycobiliproteins contained in the initial aqueous extract, preferably 75% and even more preferably 80%.

In one particular embodiment of the disclosure, said phycobiliprotein precipitate comprises at least 85% of the amount of phycobiliproteins contained in the initial aqueous extract, or at least 90%, 95% and up until the precipitation is total, i.e. said precipitate comprises 100% of the phycobiliproteins contained in the aqueous extract.

The extraction of the phycobiliproteins from a dry or fresh biomass leads to cell lysis.

The term "cell lysis" is intended to mean the rupturing of the plasma membranes of cells or of bacteria by any means and in particular physical/mechanical means (by sonication, freezing/thawing cycles) or chemical means (solutions of $CaCl_2$, $(NH_4)_2SO_4$) or else biological means (enzymes). The cell lysis generates insoluble membrane fragments and complexes which remain in suspension in the extract recovered. The removal of these extraction residues is known as clarification.

The inventors have surprisingly demonstrated that the addition of salicylic acid to an aqueous extract of phycobiliproteins makes it possible both to precipitate the phycobiliproteins contained in the extract and to remove the extraction residues.

The expression selective precipitation separating the phycobiliproteins from the extraction residues may be used. It is in fact possible to precipitate one or the other of these two groups of compounds by varying the salicylic acid concentration.

The term "clarity" is intended to mean the proportion of phycobiliproteins in the total precipitate obtained according to the process of the disclosure. The clarity is 100% when the precipitate does not contain membrane fragments that are residues of the cell lysis. After addition of the salicylic acid, the amount of unprecipitated phycobiliproteins and fragments is determined separately by spectrophotometry. The contents of precipitated phycobiliproteins and fragments is deduced therefrom. In addition, the clarity is measured in the following way: 100×amount of phycobiliproteins precipitated/(amount of phycobiliproteins+fragments precipitated).

The phycobiliprotein content is estimated on the basis of the optical density at 620 nm and 650 nm and by applying the formulae of Bryant et al. (1976). The fragment content is evaluated by measuring the optical density at 680 nm and according to a correlation curve that is established and that links the $OD_{680}$ to the dry biomass of microalgae (Costa et al., 2002).

The process according to the present disclosure makes it possible to obtain a precipitate having a phycobiliprotein content at least equal to 50% of the amount initially contained in said aqueous extract and having a clarity at least equal to 80%, preferably 90%, or equal to 100%.

The process according to the disclosure makes it possible to obtain a phycobiliprotein precipitate comprising from 50% to 80% of the amount of phycobiliproteins contained in said aqueous extract and having a clarity at least equal to 70%.

In embodiments of the disclosure, the clarity of said precipitate enriched in phycobiliproteins is equal to 75%, 80%, 85%, 90%, 95% or else 100%. In other words, the content of membrane fragments or complexes is between 0% (the clarification is then total) and 30% and can be equal to 5%, 10%, 15% or 25% of the amount of precipitate.

In embodiments of the disclosure, the process makes it possible to obtain a precipitate having a phycobiliprotein content at least equal to 70% of the amount initially contained in said aqueous extract and which is free of membrane fragments.

The term "free of membrane fragments" is intended to mean the fact that the precipitate has a clarity of 100%.

According to particular modes of the disclosure, the process according to the present disclosure uses an aqueous extract of phycobiliproteins containing at least 1.5 g/l of said phycobiliproteins.

The aqueous extract of phycobiliproteins used for the precipitation by means of salicylic acid may thus contain an amount greater than or equal to 1.5 g/l of phycobiliproteins.

The present disclosure establishes the following equation which makes it possible to determine the minimum amount of salicylic acid to be used for any amount of phycobiliproteins soluble in the initial extract.

Salicylic acid(g)=0.007×phycobiliproteins(mg)/0.52.

The salicylic acid used in the process according to the present disclosure is added to the aqueous extract containing at least 1.5 g/l of said phycobiliproteins in such a way as to obtain a salicylic acid concentration substantially greater than or equal to 4 g/l and substantially less than or equal to 20 g/l. In one particular embodiment of the disclosure, the amount of salicylic acid added is between 4 g/l and 10 g/l, or between 10 g/l and 15 g/l or else between 15 g/l and 20 g/l.

In one particular embodiment of the disclosure, the salicylic acid is added to the aqueous extract of phycobiliproteins in such a way as to obtain a salicylic acid concentration substantially greater than or equal to 4 and substantially less than or equal to 13 g/l. In this embodiment, the phycobiliprotein precipitate has a phycobiliprotein content at least equal to 50% of the initial amount contained in the aqueous extract and a clarity of 100%. In other words, the precipitate no longer exhibits membrane fragments or residues resulting from the extraction step making it possible to obtain the aqueous extract.

The clarification is then total. The membrane fragments and complexes then remain in the supernatant.

More particularly, it has been demonstrated that the quality of the clarification (total or partial clarification) is dependent on the respective contents of phycobiliproteins and of membrane fragments. Indeed, the more concentrated the solution is in terms of phycobiliproteins, and the fewer fragments it contains, the better the clarification will be. More specifically, the phycobiliprotein solution having a phycobiliprotein content greater than 1.5 g/l, preferably a phycobiliprotein content ranging from 1.5 g/l to 1.8 g/l, and a membrane fragment content ranging from 0.7 g/l to 0.9 g/l will allow good clarification. Under these conditions, the clarification may be total for a salicylic acid concentration between a value substantially greater than or equal to 4 g/l and a value substantially less than or equal to 13 g/l.

In another embodiment of the disclosure, the salicylic acid is added to the aqueous extract of phycobiliproteins in such a way as to obtain a salicylic acid concentration substantially greater than or equal to 13 g/l and substantially less than or equal to 14 g/l. In this embodiment, the phycobiliprotein precipitate has a phycobiliprotein content at least equal to 70% of the initial amount contained in the aqueous extract and a clarity at least equal to 70%.

In embodiments of the disclosure, the process may comprise a clarification step prior to the step of precipitation by salicylic acid.

The clarification may be carried out by simple decanting which removes a large portion of the residues but, under these conditions, a more or less high proportion of insoluble membrane fragments and complexes, produced from cell lysis, remains in suspension in the extract recovered.

Total clarification requires recourse to more drastic procedures such as centrifugation at more than 8000 rpm, dialysis or tangential ultrafiltration with tubes or membranes which have a cut-off of less than 100 kDaltons or chromatography using polymers which make it possible to retain the fragments during the passage of the extract. The industrial-scale extrapolation of such drastic clarification processes often generates high investment costs.

The clarification can thus be carried out by adding salicylic acid or by two complementary means, namely decantation in a first step and adding salicylic acid to the aqueous extract during the precipitation.

In embodiments of the disclosure, the process may comprise a step of dissolving the precipitate, after the selective precipitation of the phycobiliproteins using salicylic acid.

This dissolving step is in particular carried out using a natural polyol, of food quality. Glycerin or glycerol are examples thereof. Glycerin is an excellent natural preservative. It stabilizes proteins and prevents bacterial and fungal growth. Glycerin has the advantage of allowing better preservation of the phycobiliproteins.

Glycerol or any derivative or any form of the polyol propane-1,2,3-triol (or 1,2,3-propanetriol) can also be used in the context of the disclosure.

In the context of the present disclosure, it has been determined that 1.2 l of glycerin makes it possible to dissolve 27 g of precipitated and/or clarified phycobiliproteins.

The phycobiliprotein-glycerin solution can be stored for more than three months under ambient temperature and luminosity conditions and for several years in the cold and in the dark.

The process of the present disclosure can also be carried out following a step of induction of phycobiliprotein synthesis in a biomass of which the growth is blocked. The process of the present disclosure makes it possible to obtain a biomass having a phycobiliprotein content at least equal to 20% of the dry weight of said biomass.

The process of the present disclosure makes it possible in particular to obtain a biomass having a phycobiliprotein content at least equal to 21%, 22%, 23%, 24% or 25% of the dry weight of said biomass.

The process of the present disclosure makes it possible in particular to obtain a biomass having a phycobiliprotein content of between 20% and 25% of the dry weight of said biomass.

Since this synthesis step of the process is carried out outside the culture tank, it makes it possible not to impair the productivity of the biomass.

The term "biomass" is intended to mean the total mass of the living microalgae at a given moment in a culture. It is expressed in grams per liter (g/l).

The term "phycobiliproteins" is intended to mean photosynthetic water-soluble pigmentary proteins such as allophycocyanin (APC), the phycocyanin family (C-PC and R-PC), the phycoerythrin family (R-PE and C-PE) and phycoerythrocyanin (PEC), isolated from certain microalgae or from cyanobacteria.

The term "induction of the synthesis" is intended to mean the stimulation, by any means, of the production of phycobiliproteins by a biomass of microalgae.

The term "induction medium" is intended to mean any microalgae culture medium containing an excess or a deficit of one or more salts compared with the concentration of salts required for optimal growth. In the context of the disclosure, this medium contains an excess of nitrogen obtained by adding $NaNO_3$ to Zarrouk's culture medium, at a concentration greater than 2.5 g/l and preferably between 3 and 5 g/l.

The term "blocking of growth" is intended to mean stopping the multiplication of the microalga. The blocking of the growth is reversible. Indeed, following the blocking of the growth, a part of the biomass is collected. The concentration is then thus decreased and the biomass can again grow. The biomass is thus not impaired.

The step of blocking the growth of said biomass of microalgae is carried out in an induction tank, and is carried out when the concentration of said biomass in said tank is 3 to 13 times higher than the concentration which allows optimal growth of the microalgae in culture.

The blocking of the growth of said biomass of microalgae, in particular of cyanobacteria, more particularly of *Arthrospira platensis*, is carried out in an induction tank, said concentration of said biomass in said tank being in particular 3, 4, 5, 6, 7, 8, 9, 10, 11, 12 or 13 times higher than the concentration which allows the optimal growth of the microalgae in culture.

The determination of the blocking of growth (the fact that the multiplication of the microalgae is blocked) is carried out, for example, according to the curve of growth rate of the microalgae as a function of culture density. Blocking is observed when the growth rate of the microalgae is zero.

The term "concentration" can be replaced with the term "density". The terms "biomass density" or "biomass concentration" are used without distinction. The density, like the concentration, is expressed in g/l.

It is accepted that the density/concentration which allows optimal growth of the microalgae in culture is approximately 0.4 g/l.

This blocking is carried out by introducing the biomass at a concentration ranging from 1 to 5 g/l into an induction tank, but this means is not limiting and any means for blocking the growth of the biomass can be used in the context of the disclosure. The concentration of said biomass at the time of blocking can be equal to 1 g/l, 1.5 g/l, 2 g/l, 2.5 g/l, 3 g/l, 3.5 g/l, 4 g/l, 4.5 g/l or else 5 g/l.

The density/concentration of the biomass can be measured by various methods.

The Secchi disk: It is a simple device which makes it possible to rapidly estimate the density of the cells cultured in aquatic medium. It consists of a graduated ruler 30 cm long, equipped with a white disk 5 cm in diameter at the lower end, at point zero. The depth, in centimeters, starting from which it is no longer possible to distinguish the disk once immersed in the medium is noted.

Counting under a microscope. This method is time-consuming, but it makes it possible to estimate the number of filaments and the number of turns per filament. By means of a calibrated pipette, a drop of sample is deposited on a depression slide in order to observe it under a microscope; the number of filaments in a drop is evaluated, it being known that 17 drops from our pipette represent a volume of 1 ml. If the culture is very concentrated, the sample is diluted. The mean number of turn is calculated over 30 filaments taken randomly.

The optical density at 665 nm. This method makes it possible to rapidly estimate the biomass using the absorption at 665 nm, which is one of the absorption wavelengths of chlorophyll. This in vivo absorption is generally well correlated to the chlorophyll concentration. A spectrophotometer fitted with a 25 cl cuvette with parallel faces is used. Zeroing is carried out on culture medium which has not been inoculated.

The induction tank may be an intermediate culture tank or a recovery tank or any other closed system for storing living microalgae.

In one preferred embodiment of the disclosure, the concentration of said biomass in the induction tank is between a value substantially greater than or equal to 1 g/l and a value substantially less than or equal to 5 g/l. This concentration is obtained by adding induction medium to the induction tank.

The concentration ranking from 1 g/l to 5 g/l corresponds to a density from 3 to 13 times greater than the density of the biomass growing at the time of the collection, i.e. at the time of the optimal growth where the concentration is approximately 0.4 g/l. At this concentration, the growth is blocked to promote the defense metabolism of the microalga.

The growth of a biomass, for example in optimum growth, in particular at a concentration of approximately 0.4 g/l, can be blocked by bringing said biomass to a concentration of from 1 g/l to 5 g/l, for example by filtration, decanting or centrifugation.

The biomass may also undergo washing before it is deposited in the induction tank. The washing makes it possible to remove the excess salts originating from the culture medium. This thus allows better control of the nitrogen concentration of the induction solution.

In this case, the biomass is washed 3 times using a physiological water or the freshly prepared induction medium solution.

Under these conditions, the initial biomass is not affected by the process and the induction of the phycocyanin synthesis is not dependent on the biomass culture conditions.

This procedure has the advantage of being able to be easily integrated into the production line of a traditional *spirulina* culture farm. It can be applied in an intermediate culture tank or in a recovery tank for a period of 3 hours, 4 hours or up to 5 hours.

In one particular embodiment of the disclosure, the step of inducing the synthesis of the phycobiliproteins comprises:
1) exposing the biomass of photosynthetic microalgae to a light flux, said flux having a light intensity included from a value substantially greater than or equal to 10 $\mu$mol m$^{-2}$s$^{-1}$ to a value substantially less than or equal to 13 $\mu$mol m$^{-2}$s$^{-1}$;
2) adding a nitrogen source so as to obtain an NaNO$_3$ concentration in the induction medium greater than 2.5 g/l.

The light intensity in $\mu$mol of photons per square meter and per second is, for example, determined using a photometer measuring the radiation active for photosynthesis.

It should be noted that 10 $\mu$mol m$^{-2}$s$^{-1}$ correspond to 330 Lux and that 13 $\mu$mol m$^{-2}$s$^{-1}$ correspond to 429 Lux, in particular with lighting by means of a fluorescent tube, for example of "plant growth fluorescent" type. In this case, 1 $\mu$mol of photons per square meter and per second is equivalent to 33 lux.

The NaNO$_3$ concentration in the induction medium is in particular included from 3 to 4 g/l or from 3 to 5 g/l.

The combination of a light intensity included in a range of from 10 to 13 micromol m$^{-2}$s$^{-1}$ ($\mu$mol m$^{-2}$s$^{-1}$) and of a culture solution containing 3 to 5 g/l of NaNO$_3$ (as nitrogen source) makes it possible to obtain a biomass containing from 20% to 25% of phycocyanin, which is particularly high compared with the range of 3% to 12% obtained in the experiments carried out without application of the process of the disclosure.

The light can be provided by simple 40 W power incandescent lamps or by fluorescent tubes.

The preferred induction solution is made up of Zarrouk's culture medium, but any other culture medium suitable for *spirulina* can be used. In any event, the nitrogen concentration of the induction solution is modified by adding sodium nitrate (NaNO$_3$) in excess. The final concentration must be included in a range from 3 to 5 g/l of NaNO$_3$, which represents a concentration 1.2 to 2 times greater than that present in the initial Zarrouk's medium (2.5 g/l of NaNO$_3$).

Under the culture conditions defined above, the induction step is carried out for a period of 3 hours, 4 hours or up to 5 hours and is sufficient to induce phycobiliprotein synthesis at a stable content of between 20% and 25% of the dry biomass.

The process according to the disclosure, for preparing a biomass of photosynthetic microalgae having a phycobiliprotein content at least equal to 20% of the dry weight of said biomass, comprises a step of blocking the growth of the biomass and a step of inducing the synthesis of the phycobiliproteins.

According to embodiments, the biomass may have a phycobiliprotein content at least equal to 21%, 22%, 23%, 24% or 25% of the dry weight of said biomass.

According to embodiments, the biomass may have a phycobiliprotein content included from 20% to 25% of the dry weight of said biomass.

In embodiments, the step of inducing the synthesis of the phycobiliproteins can be preceded by a step of collecting a biomass of microalgae. The biomass is collected in usual culture tanks, when the culture is in the exponential growth phase, i.e. when the biomass productivity is at the maximum. The volume recovered is filtered through gauze (or by decantation or by centrifugation) in order to obtain the fresh biomass. The biomass obtained is transferred into the induction tank.

The process according to the disclosure may also comprise a final step of collecting the enriched biomass.

The process according to the disclosure may thus comprise the steps of:
a) collecting a biomass of microalgae
b) blocking the growth of said biomass
c) inducing the synthesis of the phycobiliproteins
d) collecting said biomass enriched in phycobiliproteins.

The process according to the disclosure uses photosynthetic microalgae chosen from cyanobacteria, rhodophytes or cryptophytes.

Preferably, the photosynthetic microalga used to carry out the process according to the disclosure is *Arthrospira platensis*, also called *spirulina*.

Said photosynthetic microalgae are in particular chosen from rhodophyceae, cryptophyceae and cyanobacteria, more particularly cyanobacteria, even more particularly *Arthrospira platensis* and *Aphanizomenon flos-aquae*, in particular the alga Klamath.

The present disclosure also protects a stable precipitate of phycobiliproteins as obtained by means of the process as previously described, in powder form or in suspension. The clarified and stabilized phycobiliproteins according to the disclosure can in fact be used for any application form (powder, liquid or semi-liquid) both in the cosmetics field and in the context of nutraceutical, food-processing or pharmaceutical preparations.

The phycobiliproteins precipitated using salicylic acid by means of the process of the disclosure, whether or not they are clarified beforehand by means of a decanting step, can be oven-dried at 40° C. or lyophilized, thereby improving the stability and increasing the shelf life. They can be incorporated directly into any powdered product for any food-processing, therapeutic, cosmetic or pharmaceutical application.

The precipitate dissolved and stabilized by glycerin according to the process of the disclosure can be packaged directly in vials for example or incorporated into any liquid or viscous application, as an additive, dye and active ingredient for food, cosmetic or pharmaceutical formulations.

The two forms of the phycobiliproteins as powder or in solution in glycerin contain, in addition, associated proteins, residues of the CaCl$_2$ salt that was used for the initial extraction and residues of the salicylic acid used for the precipitation. These elements are all food products which do not in any way impair the use of the product in any food, cosmetic or pharmaceutical application.

In one variant, it is possible to reduce the salt and salicylic acid content by washing the precipitate with distilled water before it is dissolved in the glycerin. This washing is preferable for applications which do not tolerate the excessive presence of salicylic acid.

The disclosure is also directed toward, as novel products, the supernatant solution obtained at the end of the precipitation and/or clarification step. This solution contains the unprecipitated fraction of phycobiliproteins and of fragments. It is moreover rich in water-soluble proteins, in trace elements and in an amount of dissolved salicylic acid. It forms a composition rich in active ingredients which can be used for any liquid form of food and/or cosmetic products.

The present disclosure also covers stable precipitates enriched in phycobiliproteins, in powder form or in suspension and totally free of membrane fragments that may be obtained by means of the process of the present disclosure.

Finally, the present disclosure protects cosmetic or nutraceutical compositions containing said stable precipitate enriched in phycobiliproteins, or a mixture of stable precipitates enriched in phycobiliproteins, whether they are compositions in powder, tablet or gel capsule form or else in liquid or viscous form such as creams, gels or pastes.

The cosmetic composition according to the present disclosure has intensive anti-wrinkle properties which make it possible to combat deep wrinkles, slackening of the skin and a dull complexion.

The cosmetic composition according to the disclosure is rich in antioxidant compounds. It acts against free radicals and stimulates cellular oxygenation. With continuous application, the contour of the face is resculpted, the deep wrinkles are reduced and the complexion is more uniform. The cosmetic composition according to the disclosure also makes it possible to reduce bags and dark circles under the eyes and protects against dehydration for better comfort.

The cosmetic composition according to the disclosure also has anti-mark effects and stimulates cell detoxification, protects against the effects of the sun and pollution, and increases the ability to combat marks characterized by an excess of melanin.

Depending on the intensity of the marks, two to four daily applications are necessary. Light and diffuse marks disappear in a few weeks, while dark marks with a defined outline may require 6 to 12 months to completely disappear. The cosmetic or dermatological composition according to the disclosure is also recommended for residual marks from heavy acne outbreaks. Moreover, it has a moisturizing effect for a supple and soft skin.

The disclosure also relates to a dermatological composition containing, as active substance, said stable precipitate enriched in phycobiliproteins, as previously defined, or a mixture of stable precipitates enriched in phycobiliproteins, and a pharmaceutically acceptable carrier.

The disclosure also relates to the use of a stable precipitate enriched in phycobiliproteins, as previously defined, or a mixture of stable precipitates enriched in phycobiliproteins, as antioxidant.

EXAMPLES

Example 1: Precipitation with Salicylic Acid

Figure 1:
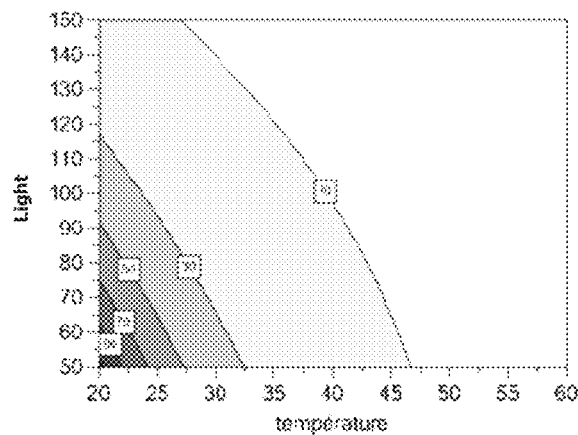
FIG. 1 represents the curve of iso-half-life of the dissolved phycobiliproteins as a function of the variation in temperature (temp in ° C.) and in light intensity (Lum in μmol photon/m$^2$/s).

The process of the present disclosure is subdivided into two essential steps:

1) Commercial grade powdered salicylic acid is added to the phycobiliprotein extract. The solution (salicylic acid+ extract) is stirred for 15 minutes. This step makes it possible to homogenize the solution and to promote the bringing of the acid into contact with the phycobiliprotein molecules in solution.

The solution is placed in a separating funnel. Virtually all of the phycobiliproteins, more than 90%, precipitate after at most one hour. The amount of salicylic acid required for the precipitation of virtually all of the phycobiliproteins after one hour depends on the amount of the latter in the initial extract. The present disclosure establishes the following equation which makes it possible to determine the minimum amount of salicylic acid to be used for any amount of soluble phycobiliproteins in the initial extract.

$$\text{Salicylic acid}(g) = 0.007 \times \text{phycobiliproteins}(mg)/0.52$$

For uses requiring a greater purity of phycobiliproteins, the disclosure shows that the phycobiliprotein extract is clarified when the selective precipitation using salicylic acid is applied. The clarification is used after a decantation step which makes it possible to remove the decantable residues from the extract. It consequently aims to separate the phycobiliproteins from the fine membrane particles which remain in the suspension after decantation.

The precipitated phycobiliproteins, possibly clarified by decantation, are recovered by coarse filtration through gauze or filter paper or simply by pouring the supernatant from the top of the separating funnel.

2) The precipitated phycobiliproteins, possibly clarified by decantation, are dissolved in glycerin. The disclosure determines that 1.2 l of glycerin are sufficient to dissolve 27 g of precipitated phycobiliproteins. The dissolution yield is between 95% and 99%. It should be pointed out that the fraction not dissolved in the glycerin can be recovered in absolute alcohol.

Example 2

The half-life of the phycobiliproteins precipitated with salicylic acid and redissolved in glycerol according to the process of the present disclosure is studied as a function of the temperature and of the light intensity.

The term "half-life" (Y) denotes the number of days resulting in the degradation of half the phycobiliproteins.

The temperature is studied in a range of 20 to 60° C., the light intensity is studied in a range of 50 to 150 μmol photon/m$^2$/s.

Eleven experiments were carried out, including eight representing the combination between the three levels corresponding to the two factors. The other three represent central points and make it possible to evaluate the experimental error.

The mathematical model proposed is:

$$\text{Log}_{10} Y = 4 - 0.08 \text{Temp} - 0.013 \times Lum + 0.0005 \times \text{Temp}^2 + 0.0002 \times \text{temp} \times Lum.$$

This model is valid at 94%, with a correlation coefficient $R^2 = 98\%$ and is predictable (Q) at 95%.

The variation in the half-life of the phycobiliproteins (in days) according to the temperature and light conditions is given by the iso half-life curve (FIG. 1).

The half-life of the phycobiliproteins precipitated with salicylic acid and redissolved in glycerol can exceed 110 days, for a temperature below 20° C. and a light intensity below 50 μmol photon/m$^2$/s.

By prediction outside the study range, it is possible to estimate the half-life of the stabilized phycobiliproteins at 11 years when the storage conditions are 4° C. and in total darkness.

Under the same temperature (20° C.) and luminosity (50 µmol photon/m$^2$/s) conditions, the stability tests show that, for the untreated aqueous extracts, i.e. those which have not been subjected to the process of the disclosure based on the addition of salicylic acid and/or glycerin, all of the phycobiliproteins are degraded after 12 hours. For the powdered phycobiliproteins, precipitated and stabilized with salicylic acid without redissolving in glycerin, the degradation does not exceed 10% after more than 2 months of incubation.

For the aqueous extracts dissolved in glycerin but not precipitated with salicylic acid according to the process of the present disclosure, the degradation is 50% after one month of incubation.

The aqueous extracts precipitated with salicylic acid and dissolved in glycerin show better stability.

Example 3

It is sought to clarify the extracted phycobiliproteins by selective precipitation with salicylic acid. The extraction can be carried out from dry or fresh *spirulina* biomass.

13 g of dry *spirulina* (or 130 g of fresh *spirulina*) are used, suspended in 0.2 l of sterile sea water, well homogenized.

The whole mixture is frozen at −4° C. overnight. It is thawed in 0.4 l of sterile sea water and subjected to stirring for two hours under cold conditions. A second freezing-thawing followed by thawing in 0.4 l of sterile sea water with stirring under cold conditions for two hours is carried out.

The suspension obtained is transferred into a decanting receptacle overnight under cold conditions in order to separate the aqueous phase of the extract, from the decantable biomass.

The phycobiliprotein extraction yield is estimated at 12-15% of the dry weight of the *spirulina*.

The phycobiliprotein content is estimated on the basis of the optical density at 620 nm and 650 nm and by applying the formulae of Bryant et al. (1976). The fragment content is evaluated by measuring the optical density at 680 nm according to an established correlation curve linking the OD680 to the dry *spirulina* biomass.

The phycobiliprotein concentration of the extract, thus evaluated, is 1.5 g/l of sea water.

The content of fragments and of membrane elements is evaluated at 1.9 g/l.

1 to 2 g of powdered salicylic acid are intermittently added with continuous stirring.

At each addition, the solution is left to stand for two hours, after which time the phycobiliproteins precipitate. The amount of phycobiliproteins and of fragments in solution is then evaluated in order to determine the degrees of precipitation.

Figure 2:
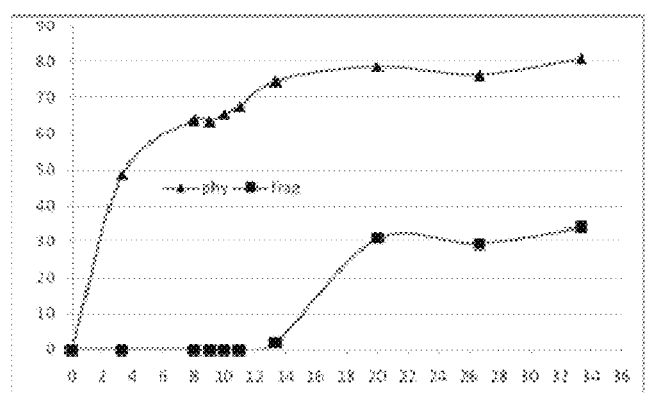
FIG. 2 represents the variation in the degree of precipitation of the phycobiliproteins (phy) and of the fragments (frag) as a function of the salicylic acid concentration (g/l).

The results of the degrees of precipitation are presented in FIG. 2.

It is shown that it is possible to obtain a 100% clarified precipitate for a concentration of less than 12-13 g/l of salicylic add.

The maximum yield of precipitated and totally clarified phycobiliproteins thus obtained is 70% for an addition of 13 g/l of salicylic acid.

All of the membrane fragments and complexes remain in the supernatant and are only precipitated at high concentrations of salicylic acid.

Example 4: Variation in the Level of Clarity of the Precipitated Phycobiliproteins The variation in the level of clarity of the precipitated phycobiliproteins is studied for various initial phycobiliprotein and fragment concentrations in the extract (obtained by various dilution and centrifugation) and for various salicylic acid concentrations.

The study is carried out according to the experimental design methodology, by means of a complete factorial design having three levels with interaction. The factors are: the initial phycobiliprotein concentration of the extract, ranging from 0.3 to 1.52 g/l, the fragment concentration ranging from 0.7 to 1.9 g/l and the salicylic acid concentration in a range of 10 to 20 g/l.

The experimental matrix given by the model is composed of fifteen experiments representing the combination between the three levels (minimum, maximum and center) corresponding to the three factors. Three repetitions of the same combination make it possible to evaluate the experimental error.

After addition of the salicylic acid, the amount of phycobiliproteins and of fragments not precipitated is determined separately for each experiment by spectrophotometry. The contents of precipitated phycobiliproteins and fragments are deduced therefrom. The clarity is calculated.

"Clarity" is denoted by clarity=100×amount of precipitated phycobiliproteins/amount of precipitated phycobiliproteins+fragments.

Figure 3:
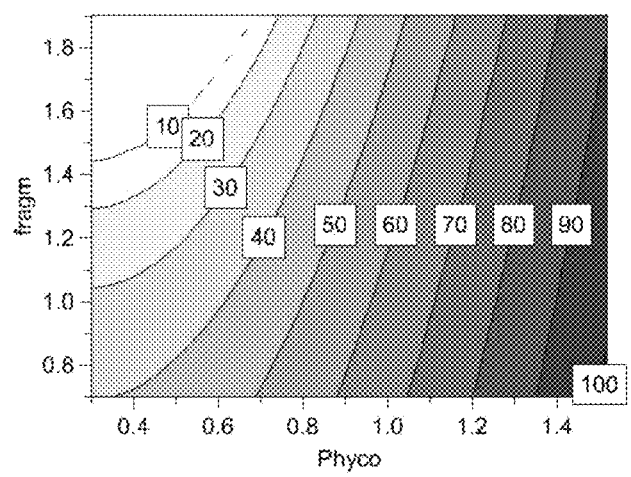
FIG. 3 represents the variation in the clarity of the precipitate as a function of the concentration of fragments (g/l) and of the initial concentrations of phycobiliproteins. The salicylic acid content is 13 g/l.

The model makes it possible to plot the iso-clarity curves that are presented in FIG. 3.

It is shown that it is possible to obtain a level of total clarification of 100% only for a phycobiliprotein concentration greater than 1.5 g/l and a fragment content less than 0.9 g/l. The salicylic acid content required for total clarification under these conditions is less than 13 g/l.

Example 5: Anti-Wrinkle Cream

An anti-wrinkle cream is obtained with the following composition:
Water: 59%,
Sweet almond oil: 18%,
Stable precipitate enriched in phycobiliproteins dissolved in glycerin: 7%,
Palm oil: 5%, Castor oil: 3%,
Extract of algae: 3% (beta-carotene),
Beeswax: 2%,
Xanthan gum: 1.7%,
Fragrance: 1%,
Ethyl paraben: 0.1%, methyl paraben: 0.1%, benzyl paraben: 0.1%.

Example 6: Anti-Mark Cream

An anti-mark cream is obtained with the following composition:
Anti-mark cream:
Water: 59%,
Sweet almond oil: 19.5%,
Stable precipitate enriched in phycobiliproteins dissolved in glycerin: 7%,
Palm oil: 5%, Castor oil: 3%, Extract of algae: 1.5% (beta-carotene),
Beeswax: 2%,
Xanthan gum: 1.7%,
Fragrance: 1%,
Ethyl paraben: 0.1%, methyl paraben: 0.1%, benzyl paraben: 0.1%.

REFERENCES

Arad and Ai., 1997. Coloring material. U.S. Pat. No. 5,643,585
Bryant D. A., Glazer, A. N. and Eiserling F. A., 1976. Characterisation and Structural properties of the major biliproteins of *Anabaena* sp. *Arch. Microbiol,* 110, 61-75.
Costa J A V, Colla L M, Duarte Filho P F, Kabke K, Weber A., 2002. Modelling of *Spirulina platensis* growth in freshwater using response surface methodology. World J Microbiol Biotechnol 18:603-607
Minard. F., 2005. Method for the photostabilisation of phycobiliproteins in an aqueous extract, compositions containing stabilised phycobiliproteins and use of stabilised phycobiliproteins. Patent No. WO2005065697 A1.
Rebeller M. Yout P and Lonchamp D., 1979. Procédé d'extraction selective des colorants contenus dans les algues cyanophycdes [Process for selective extraction of dyes contained in cyanophyceae algae]. (Patent filed by the Institut français du pétrole entered under classification C 09 B 61/00).
Frédéric Pottecher, 2014. Procédé d'extraction et de stabilisation dephycocyanine et ses application [Process for extraction and stabilization of phycocyanin and applications thereof]. WO 2014045177 A1. Patent filed by Ecosystem.

The invention claimed is:

1. A process for obtaining a stable precipitate enriched in phycobiliproteins, comprising at least one precipitation step consisting of adding salicylic acid to an aqueous extract of phycobiliproteins to precipitate the phycobiliproteins, said precipitate having a phycobiliprotein content at least equal to 50% of the amount initially contained in said aqueous extract, and said precipitate having a clarity at least equal to 70%, and
wherein the salicylic acid precipitates the phycobiliproteins and is added to the aqueous extract of phycobiliproteins to obtain a salicylic acid concentration in a range of from 4 g/l to 20 g/l.

2. The process as claimed in claim 1, wherein said precipitate has a phycobiliprotein content at least equal to 50% of the amount initially contained in said aqueous extract and said precipitate has a clarity at least equal to 80%.

3. The process as claimed in claim 1, wherein said precipitate has a phycobiliprotein content at least equal to 70% of the amount initially contained in said aqueous extract and is free of membrane fragments.

4. The process as claimed in claim 1, wherein said aqueous extract of phycobiliproteins contains at least 1.5 g/l of said phycobiliproteins.

5. The process as claimed in claim 1, wherein the salicylic acid is added to the aqueous extract of phycobiliproteins to obtain a salicylic acid concentration in a range of from 4 g/l to 13 g/l.

6. The process as claimed in claim 1, wherein the salicylic acid is added to an aqueous extract of phycobiliproteins to obtain a salicylic acid concentration in a range of from 13 to 14 g/l.

7. The process as claimed in claim 1, wherein a step of clarification by decanting is performed prior to the step of precipitation by salicylic acid.

8. The process as claimed in claim 1, wherein a step of dissolving the precipitate is performed.

9. The process as claimed in claim 8, wherein the precipitate is dissolved in a natural polyol chosen from glycerin, glycerol, or any derivative or any form of a polyol propane-1,2,3-triol (or 1,2,3-propanetriol).

10. The process as claimed in claim 1, which comprises, beforehand, a step of enrichment in phycobiliproteins of a biomass of photosynthetic microalgae.

11. The process as claimed in claim 10, wherein the prior step of enrichment in phycobiliproteins comprises an induction of the phycobiliprotein synthesis in a biomass of which the growth is blocked.

12. The process as claimed in claim 1, which further comprises:
   a. a step of blocking the growth of a biomass of photosynthetic algae, and
   b. a step of inducing the synthesis of the phycobiliproteins,
   wherein step a and step b are carried out prior to the at least one precipitation step, and
   c. a step of dissolving the precipitate obtained from the at least one precipitation step.

13. The process as claimed in claim 1, wherein the aqueous extract of phycobiliproteins is obtained from *Arthrospira platensis* photosynthetic microalgae.

* * * * *